(12) United States Patent
Schaeffer et al.

(10) Patent No.: US 10,105,216 B2
(45) Date of Patent: Oct. 23, 2018

(54) VOCAL CORD MEDIALIZATION

(71) Applicant: Cook Medical Technologies LLC, Bloomington, IN (US)

(72) Inventors: Darin Schaeffer, Bloomington, IN (US); Pamela Ridgley, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 15/254,621

(22) Filed: Sep. 1, 2016

(65) Prior Publication Data

US 2017/0172734 A1 Jun. 22, 2017

Related U.S. Application Data

(63) Continuation of application No. 14/270,802, filed on May 6, 2014, now Pat. No. 9,433,499.

(60) Provisional application No. 61/820,234, filed on May 7, 2013.

(51) Int. Cl.
*A61F 2/20* (2006.01)

(52) U.S. Cl.
CPC ........ *A61F 2/20* (2013.01); *A61F 2230/0017* (2013.01); *A61F 2230/0091* (2013.01)

(58) Field of Classification Search
CPC .............................. A61F 2/20; A61F 2002/206
See application file for complete search history.

(56) References Cited

U.S. PATENT DOCUMENTS

| D200,283 S | 2/1965 | Gershen |
| 4,052,754 A | 10/1977 | Homsy |
| 4,094,303 A | 6/1978 | Johnston |
| 4,269,192 A | 5/1981 | Matsuo |
| 4,281,669 A | 8/1981 | Mac Gregor |

(Continued)

FOREIGN PATENT DOCUMENTS

| EP | 0453186 | 11/1991 |
| EP | 0856299 | 8/1998 |

(Continued)

OTHER PUBLICATIONS

International Search Report (PCT/ISA/210) for PCT/FR2008/000262 dated Sep. 1, 2008.

(Continued)

*Primary Examiner* — Thomas J Sweet
*Assistant Examiner* — Daniel Bissing
(74) *Attorney, Agent, or Firm* — Buchanan Van Tuinen LLC

(57) ABSTRACT

Medical devices, medical device kits, and related methods of treatment are described. An exemplary medical device comprises a proximal portion having an outer surface defining a thread and an inner surface defining a passageway having a keyed portion, a distal portion providing an atraumatic tip, and a flexible main body extending between the proximal portion and the distal portion. The medical device can be positioned in contact with a paralyzed vocal cord to cause a desired medialization for treatment of the vocal cord. The flexible main body allows for deflection upon contact and/or interaction with another device passed into the airway of a treated patient.

2 Claims, 5 Drawing Sheets

(56) References Cited

U.S. PATENT DOCUMENTS

| | | |
|---|---|---|
| 4,374,669 A | 2/1983 | Mac Gregor |
| 4,550,448 A | 11/1985 | Kenna |
| D284,507 S | 7/1986 | Leopoldi |
| 4,744,792 A | 5/1988 | Sander et al. |
| 4,745,910 A | 5/1988 | Day et al. |
| 4,863,476 A | 9/1989 | Shepperd |
| 4,938,234 A | 7/1990 | Capriotti |
| 5,197,482 A | 3/1993 | Rank et al. |
| 5,197,982 A | 3/1993 | Goldsmith et al. |
| 5,201,765 A | 4/1993 | Netterville et al. |
| 5,306,298 A * | 4/1994 | Godley, III ............... A61F 2/20 623/9 |
| 5,326,375 A | 7/1994 | Montgomery et al. |
| 5,344,452 A | 9/1994 | Lemperle |
| 5,344,453 A | 9/1994 | Montgomery et al. |
| 5,358,522 A | 10/1994 | Montgomery et al. |
| 5,360,448 A | 11/1994 | Thramann |
| 5,376,076 A | 12/1994 | Kaali |
| 5,437,266 A | 8/1995 | McPherson et al. |
| 5,531,752 A | 7/1996 | Netterville et al. |
| 5,549,673 A | 8/1996 | Beale |
| 5,593,439 A | 1/1997 | Cummings et al. |
| 5,693,096 A | 12/1997 | Bettez et al. |
| 5,855,607 A | 1/1999 | Friedrich |
| 6,123,710 A | 9/2000 | Pinczewski et al. |
| 7,025,784 B1 | 4/2006 | Blom et al. |
| 9,084,675 B2 | 7/2015 | Eller et al. |
| 9,433,499 B2 | 9/2016 | Schaeffer et al. |
| 2004/0254642 A1 | 12/2004 | Isshiki et al. |
| 2005/0154390 A1 | 7/2005 | Biedermann et al. |
| 2006/0200151 A1 | 9/2006 | Ducharme et al. |
| 2008/0023012 A1 | 1/2008 | Dineen et al. |
| 2008/0071230 A1 | 3/2008 | Lindenthaler |
| 2009/0044814 A1 | 2/2009 | Iancea et al. |
| 2010/0023125 A1 | 1/2010 | Debry et al. |
| 2011/0301580 A1 | 12/2011 | Hoffman |
| 2012/0055492 A1 | 3/2012 | Nikolchev et al. |
| 2012/0150293 A1 | 6/2012 | Hoffman et al. |
| 2012/0158137 A1 | 6/2012 | Pinczewski |
| 2013/0123794 A1* | 5/2013 | Walker ............... A61B 17/10 606/104 |
| 2013/0131733 A1 | 5/2013 | Chien et al. |
| 2013/0303848 A1 | 11/2013 | Kahle et al. |
| 2014/0058509 A1 | 2/2014 | Ridgley et al. |
| 2014/0100612 A1 | 4/2014 | Suddaby |
| 2014/0195245 A1 | 7/2014 | Eller et al. |
| 2014/0336761 A1 | 11/2014 | Schaeffer et al. |
| 2017/0172734 A1 | 6/2017 | Schaeffer et al. |

FOREIGN PATENT DOCUMENTS

| | | |
|---|---|---|
| FR | 2758974 | 8/1998 |
| WO | WO9006093 | 6/1990 |
| WO | WO9221303 | 12/1992 |

OTHER PUBLICATIONS

Written Opinion (PCT/ISA/237) for PCT/FR2008/000262 dated Sep. 1, 2008.

European Patent Office, Partial European Search Report, Patent App. No. 13181629, dated Nov. 22, 2013, pp. 1-5.

File history of U.S. Appl. No. 13/201,669, as of Aug. 11, 2014. Filed Aug. 16, 2011. First Named Inventor, Henry T. Hoffman. Title, Methods and devices for arytenoid repositioning.

Hoffman, Henry T., et al., "Arytenoid Repositioning Device," Annals of Otology, Rhinology & Laryngology, Mar. 2014, vol. 123, Issue 3, pp. 195-205.

United States Patent and Trademark Office, Office Action for U.S. Appl. No. 13/974,451, dated Mar. 24, 2015, pp. 1-12.

* cited by examiner

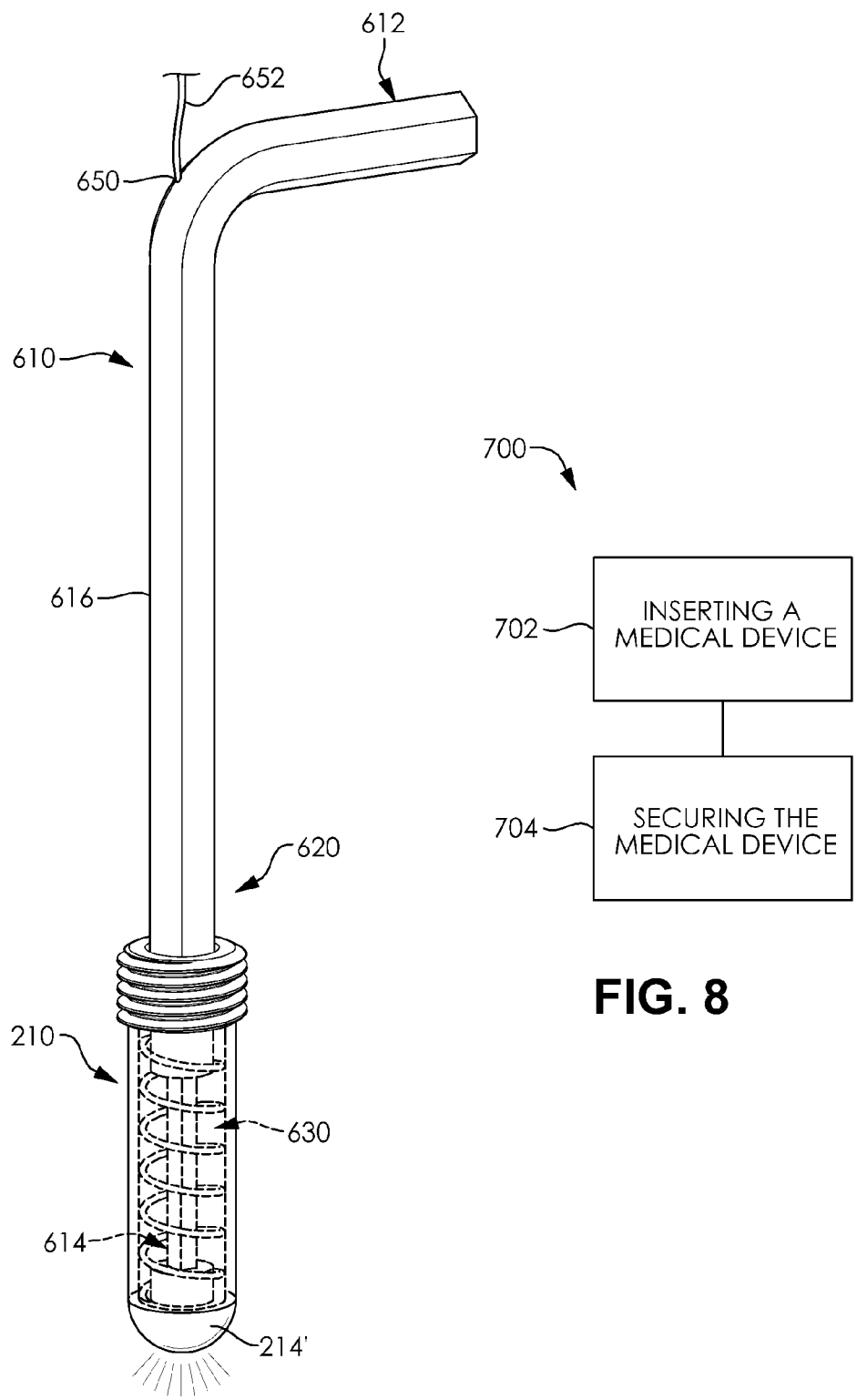

VOCAL CORD MEDIALIZATION

RELATED APPLICATIONS

This application is a continuation of U.S. patent application Ser. No. 14/270,802, filed on May 6, 2014, which claims the benefit of U.S. Provisional Application No. 61/820,234, filed on May 7, 2013. The disclosure of each of these related applications is hereby incorporated into this disclosure in its entirety.

FIELD

The disclosure relates generally to the field of implantable medical devices. More particularly, the disclosure relates to implantable medical devices, medical device kits, and related methods useful in the medialization of the vocal cords.

BACKGROUND

The vocal cords, or vocal folds, are a pair of bands or folds of mucous membrane in the throat that stretch across the larynx. The cords are abducted, or open, during inhalation and adducted, or closed, when holding one's breath with an open mouth. During phonation, a rhythmic abduction and adduction of the cords allows the larynx to generate sounds for speech, singing and other vocalizations.

Vocal cord dysfunction can occur when one or both of the cords becomes paralyzed and recedes into a permanently open position. Vocal cord paralysis greatly impacts the afflicted individual's quality of life as it negatively affects their ability to communicate effectively. Various treatments for vocal cord paralysis have, therefore, been developed over the years.

Various implantable medical devices for medializing—moving toward the midline of the body—are known. While some of these devices may be effective in moving a paralyzed cord, none of the known devices adequately address the need for an implantable medical device that is effective in moving a paralyzed vocal cord while being able to accommodate the passage of other items, such as other medical devices, into or through the trachea. For example, the unyielding nature of prior art vocal cord implant devices can present a safety concern when a conduit is passed into the trachea during a typical intubation procedure.

Thus, a need exists for improved medical devices, kits and methods useful in the treatment of paralyzed vocal cords.

BRIEF SUMMARY OF DESCRIBED EMBODIMENTS

Various exemplary medical devices, medical device kits and methods useful in the treatment of paralyzed vocal cords are described and illustrated herein.

An exemplary medical device comprises a proximal portion having a proximal portion outer surface defining a thread and a proximal portion inner surface comprising a series of facets and defining a proximal passageway extending through the proximal portion; a distal portion having a distal portion outer surface defining an atraumatic distal tip and a distal portion inner surface; and a flexible main body extending between the proximal portion and the distal portion and defining a main passageway in communication with the proximal passageway.

Another exemplary medical device comprises a proximal portion having a proximal portion outer surface defining a thread and a proximal portion inner surface comprising a series of facets and defining a proximal passageway extending through the proximal portion; a distal portion having a distal portion outer surface defining an atraumatic distal tip and a distal portion inner surface; and a flexible main body extending between the proximal portion and the distal portion, the main body comprising a tubular member defining a main passageway and a helical member disposed within the main passageway, the main passageway in communication with the proximal passageway.

Another exemplary medical device comprises a proximal portion having a proximal portion outer surface defining a thread and a proximal portion inner surface defining a proximal passageway extending through the proximal portion, the proximal portion inner surface having a first series of facets defining a first keyed portion of the proximal passageway and a second series of facets defining a second keyed portion of the proximal passageway, the proximal portion further defining a proximal stanchion; a distal portion having a distal portion outer surface defining an atraumatic distal tip and a distal portion inner surface defining a distal stanchion; and a flexible main body extending between the proximal portion and the distal portion, the main body comprising a tubular member defining a main passageway and a helical member disposed within the main passageway and in engagement with the proximal stanchion and the distal stanchion, the main passageway in communication with the proximal passageway.

Additional understanding of the inventive medical devices, kits, and methods can be obtained with review of the detailed description, below, and the appended drawings.

BRIEF DESCRIPTION OF THE DRAWINGS

FIG. 7 is a perspective view of an alternative implant assembly including the medical device illustrated in FIG. 3 and an engaged alternate insertion tool.

FIG. 8 is a flowchart illustrating an exemplary method of use.

DETAILED DESCRIPTION OF ILLUSTRATED EMBODIMENTS

As used herein, the term "exemplary" refers to the property of being an example; the term does not refer to a relative level of performance or preference of one or more examples as compared to others.

The following detailed description and the appended drawings describe and illustrate various exemplary medical devices, medical device kits, and related methods of use. The description and drawings are exemplary in nature and are provided to enable one skilled in the art to make and use one or more exemplary medical devices, kits and/or to practice one or more exemplary methods. They are not intended to limit the scope of the claims in any manner.

Figure 1:
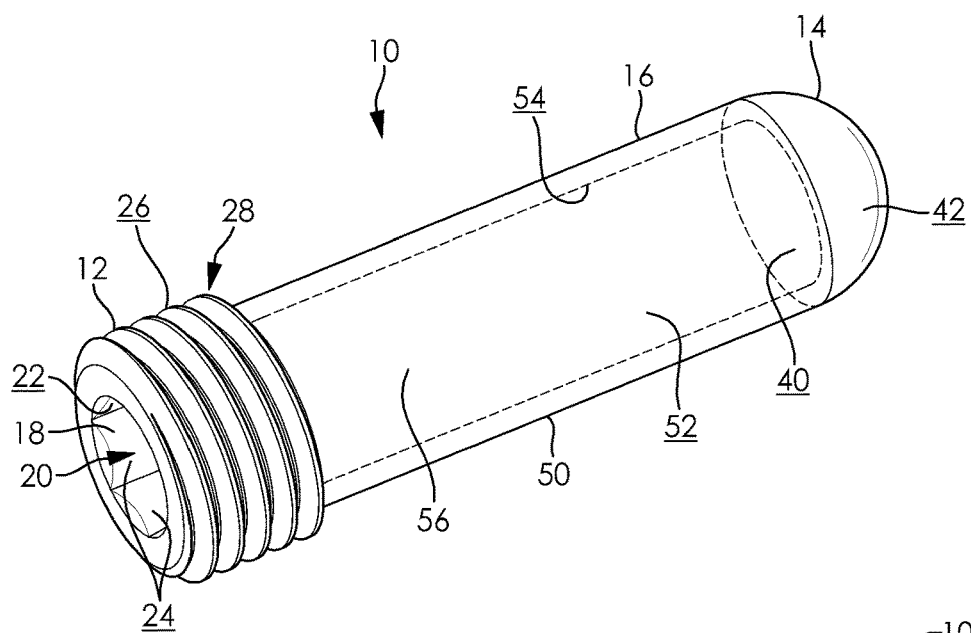
FIG. 1 is a perspective view of a first exemplary medical device.
Figure 1A:
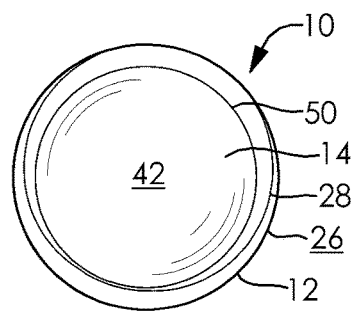
FIG. 1A is an end view of the medical device illustrated in FIG. 1.

FIGS. 1 and 1A illustrate a first exemplary medical device 10. The medical device 10 includes a proximal portion 12, a distal portion 14, and a main body 16 that extends along the lengthwise axis of the medical device 10 and between the proximal 12 and distal 14 portions. Main body 16 is in contact with each of the proximal 12 and distal 14 portions.

A proximal portion 12 defines a proximal opening 18 and a proximal passageway 20 that extends through the proximal portion 12 along the lengthwise axis of the medical device 10. While the illustrated embodiment includes a proximal passageway 20 that extends through the entire proximal portion 12, it is noted that a proximal passageway that extends through a portion of the proximal portion 12 can be used. Indeed, examples of suitable proximal passageways include a proximal passageway that extends through only a portion of the proximal portion 12, a proximal passageway that extends through at least a portion of the proximal portion 12, and a proximal passageway that extends through the entire proximal portion 12. An inner surface 22 of the proximal portion 12 defines a series of facets 24. An outer surface 26 of proximal portion 12 defines a thread 28.

The distal portion 14 defines an inner surface 40 and an outer surface 42. In the illustrated embodiment, the inner surface 40 is a flat surface that extends along a plane disposed orthogonally to the lengthwise axis of the medical device 10. Alternatively, the inner surface 40 can be a substantially flat surface and/or can define or include structure for receiving and/or engaging a portion of the main body 16, as described below. For example, the inner surface 40 can define a circumferential channel or circumferential shoulder for receiving the circumferential wall of the main body 16. The outer surface 42 defines a rounded surface to provide an atraumatic distal tip to the medical device 10. In the illustrated embodiment, the outer surface 42 defines a hemispherical surface. It is understood, however, that the outer surface 42 can have any suitable configuration, including flat, substantially flat, and non-hemispherical rounded configurations.

The main body 16 comprises a circumferential wall 50 having an outer surface 52, an inner surface 54, and that defines a main passageway 56. The main passageway 56 extends through the main body 16 such that it is in communication with proximal passageway 20 of the proximal portion 12 and terminates at the inner surface 40 of the distal portion 14. This configuration of the passageway 56 is optional, though, and a passageway that is separate from the proximal passageway 20 of the proximal portion 12 can also be used. The main body 16 is in contact with the proximal 12 and distal 14 portions. Furthermore, the main body 16 is secured to the proximal 12 and distal 14 portions. The securement of these elements to each other can be accomplished in any suitable manner and a skilled artisan will be able to select an appropriate manner for a medical device according to a particular embodiment based on various considerations, such as the nature of the materials used for each of the elements. For example, the main body 16 can be secured to the proximal 12 and distal 14 portions using adhesives, mechanical engagements, welds, and other suitable manners for securing elements to each other.

Each of the elements of the medical device 10 can be made from any suitable material and a skilled artisan will be able to select appropriate materials for medical device according to a particular embodiment based on various considerations, including the desired properties of each element. The materials selected need only be biocompatible or be capable of being rendered biocompatible.

The proximal portion 12 is advantageously relatively rigid as compared to the main body 16 as it serves as an anchor for the medical device 10 in tissue of the patient being treated. For example, in the illustrated embodiment, the thread 28 can be used to anchor the medical device 10 in cartilage. As such, examples of suitable materials for the proximal portion 12 include relatively rigid materials, such as metals, plastics and ceramic materials.

In contrast, the distal portion 14 is advantageously relatively soft and atraumatic as it can contact the vocal cord during placement and use. as such, examples of suitable materials for the distal portion 14 include polymeric materials, such as polyethylene, polypropylene, polyurethane, and nylon.

The main body 16 is advantageously a flexible member that allows for deflection upon contact and/or interaction with another device, as described below. As such, examples of suitable materials for the main body 16 include polymeric materials, such as polyethylene, polypropylene polyurethane, nylon, and polyether block amides; and metals, such as spiral cut metal tubing, including Nitinol and stainless steel tubing.

Figure 2:
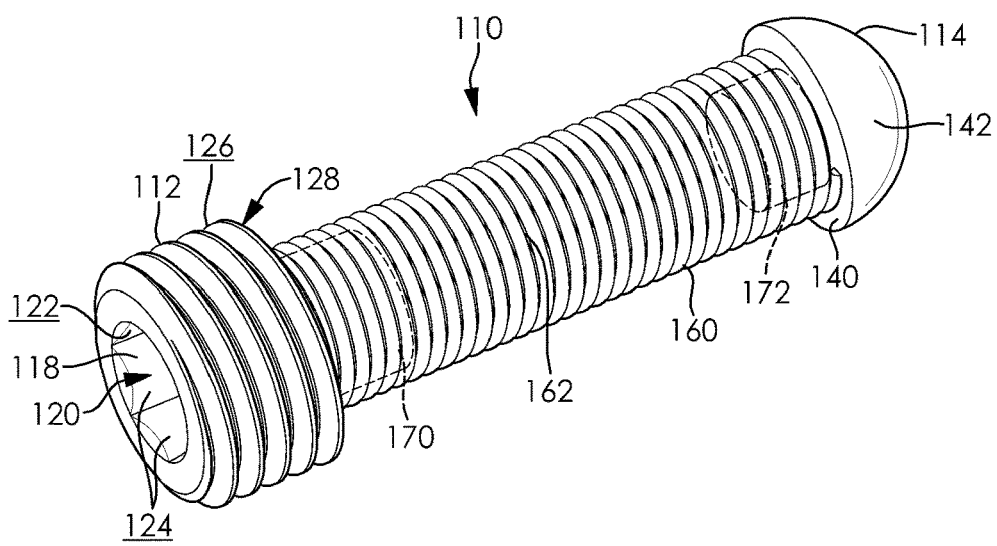
FIG. 2 is a perspective view of a second exemplary medical device.

FIG. 2 illustrates a second exemplary medical device 110. The medical device 110 of this embodiment is similar to medical device 10 illustrated in FIGS. 1 and 1A and described above, except as detailed below. Thus, medical device 110 includes a proximal portion 112 and a distal portion 114. The proximal portion 112 defines an opening 118 and a proximal passageway 120 that extends through the proximal portion 112 and along the lengthwise axis of the medical device 110. This configuration of the proximal passageway 120 is optional, though, and a passageway that extends through only a portion of the proximal portion 112 can also be used. An inner surface 122 of the proximal portion 112 defines a series of facets 124. An outer surface 126 of proximal portion 112 defines a thread 128. The distal portion 114 defines an inner surface 140 and the rounded outer surface 142 that provides an atraumatic distal tip for the medical device 110.

In this embodiment, the main body 160 comprises a helical member that extends along the lengthwise axis of the medical device 110 and between the proximal 112 and distal 114 portions. The main body 160 defines a main passageway 162 that extends along the lengthwise axis of the medical device 110 in between the proximal 112 and distal 114 portions. In contrast to the medical device 10 according to the first exemplary embodiment, the main passageway 162 is not a closed passageway. Rather, the main passageway 162 is open to the environment external to the medical device 110. This structure can be advantageous in situations in which it is desired to allow cellular ingrowth to occur following implantation of the medical device 110. In contrast, the structure illustrated and described for the first exemplary medical device 10 can be advantageous in situations in which such cellular ingrowth is not desired. In both embodiments, however, the main body comprises a flexible structure that confers the desired deflectability onto the medical device.

The main body 160 can comprise any suitable helical member, including a spring. Examples of suitable helical members include an extension spring, such as the main body 160 illustrated in FIG. 2, and a coil compression spring.

In this embodiment, the main body 160 is secured to the proximal 112 and distal 114 portions via a mechanical engagement. The proximal portion 112 defines a proximal stanchion 170 that extends into the main passageway 162. Similarly, the distal portion 114 defines a distal stanchion 172 that extends into the main passageway 162 in the opposite direction. Each of the proximal 170 and distal 172 stanchions is advantageously in mechanical engagement with the helical member of the main body 160. For example, the helical member of the main body 160 is advantageously friction fit over the proximal 170 and distal 172 stanchions. It is understood, though, that the main body 160 can be secured to the proximal 112 and distal 114 portions and other suitable manners, as described above. For example, in addition to or as an alternative to, an adhesive can be used to secure the helical member of the main body 160 on to the proximal 170 and distal 172 stanchions. Furthermore, one or both of the proximal 170 and distal 172 stanchions can define additional structure adapted to receive a portion of the helical member of the main body 160, such as a helical channel extending along an outer surface of the stanchion 170, 172. Furthermore, two or more of the proximal portion 112, distal portion 114, and the main body 160 could be made as a single component. For example, distal portion 114 and main body 160 could comprise a single molded component.

FIGS. 3, 3A, 3B, and 3C illustrate a third exemplary medical device 210. The medical device 210 of this embodiment shares elements and features with the medical device 10 of the first exemplary embodiment and the medical device 110 of the second exemplary embodiment, and includes additional features and structure, as described below. Thus, medical device 210 includes a proximal portion 212 and a distal portion 214. The proximal portion 212 defines an opening 218 and a proximal passageway 220 that extends through the proximal portion 212 and along the lengthwise axis of the medical device 210. An inner surface 222 of the proximal portion 212 defines a series of facets 224. An outer surface 226 of proximal portion 212 defines a thread 228. The distal portion 214 defines an inner surface 240 and a rounded outer surface 242 that provides an atraumatic distal tip for the medical device 210.

In this embodiment, the main body 280 comprises a helical member 282 and a tubular member 284 having a circumferential wall 286. The helical member 282 is disposed within the tubular member 284 such that, together, the helical member 282 and tubular member 284 cooperatively define main passageway 288 that extends along the lengthwise axis of the medical device 210 in between the proximal 212 and distal 214 portions. This structural arrangement is considered advantageous at least because the helical member 282 confers flexibility and resiliency on to the main body 280 while the tubular member 284 provides a barrier to prevent cellular ingrowth into the main passageway 288.

As with the embodiment illustrated in FIG. 2, the helical member 282 of the main body 280 can comprise any suitable helical member, including a spring. Examples of suitable helical members include a compression spring, such as the helical member 282 illustrated in FIG. 3, and an extension spring.

In this embodiment, the main body 280 is secured to the proximal 212 and distal 214 portions via both a mechanical engagement between the helical member 282 and the proximal 212 and distal 214 portions, and a securement between the tubular member 284 and the proximal 212 and distal 214 portions. Similar to the medical device 110 illustrated in FIG. 2 and described above, the helical member 282 is in mechanical engagement with a proximal stanchion 270 defined by the proximal portion 212 and a distal stanchion 272 defined by the distal portion 214. Also, the tubular member 284 is secured to the proximal 212 and distal 214 portions. The structure of this embodiment is also considered advantageous at least because of the additional securement between the components 282, 284 of the main body 280 and the proximal 212 and distal 214 portions.

Figure 3:
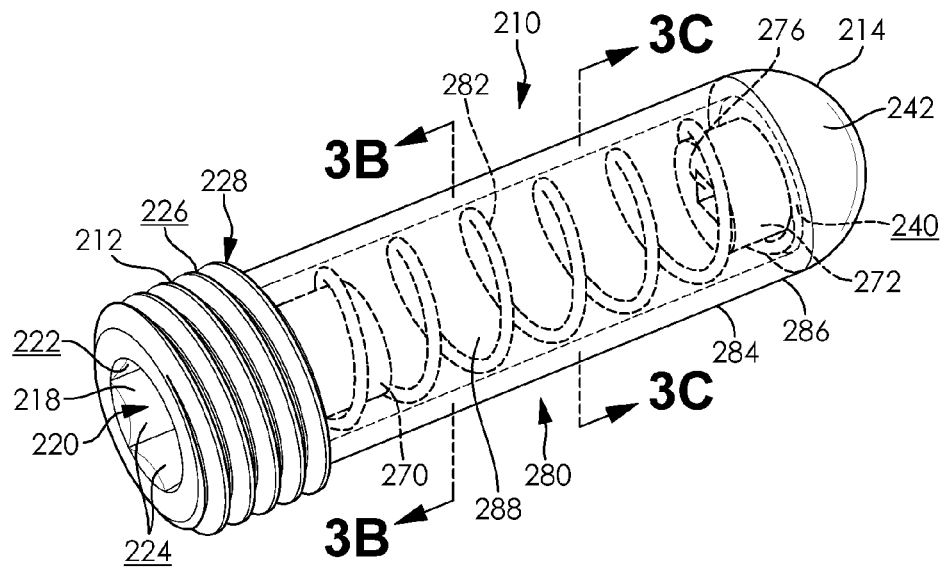
FIG. 3 is a perspective view of a third exemplary medical device.
Figure 3A:
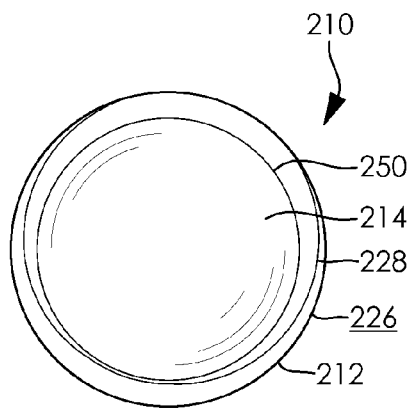
FIG. 3A is an end view of the medical device illustrated in FIG. 3.
Figure 3B:
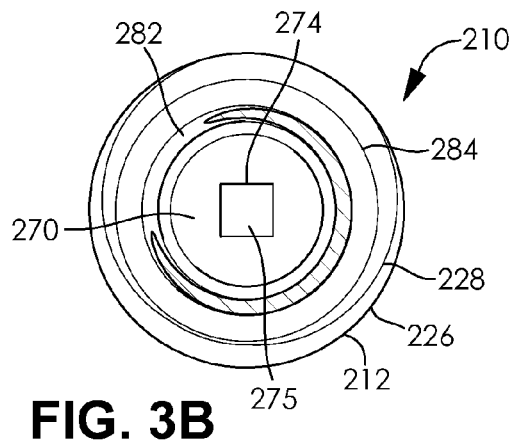
FIG. 3B is a sectional view of the medical device illustrated in FIG. 3, taken along line 3B-3B.
Figure 3C:
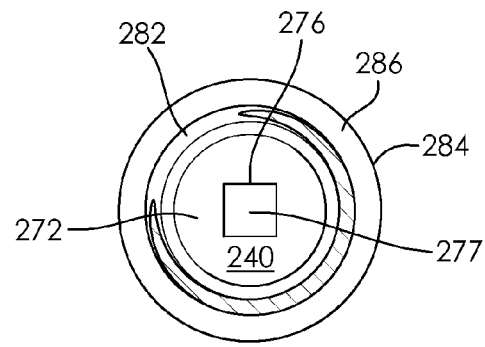
FIG. 3C is a sectional view of the medical device illustrated in FIG. 3, taken along line 3C-3C.

As best illustrated in FIG. 3B, the proximal stanchion 270 defines a keyed portion 274 of the proximal passageway 220. The keyed portion 274 provides structure for mechanical engagement with an insertion tool, as described below. The keyed portion 274 of the proximal passageway 220 can have any suitable size and configuration and a skilled artisan will be able to select an appropriate size and configuration for a medical device according to a particular embodiment based on various considerations, including the configuration of any insertion tool with which the medical device will be used. In the illustrated embodiment, the keyed portion 274 of the proximal passageway 220 defines a square—shaped opening 275. The illustrated keyed portion 274 would be suitable for use with an insertion tool having a projection defining a complimentary square-shaped cross-sectional profile, i.e., a projection that can pass through the opening 275 defined by the keyed portion 274 and that can mechanically engage each of the sidewalls of the keyed portion 274 of the proximal passageway. Other exemplary configurations for the keyed portion 274 of the proximal passageway 220 include rectangular, triangular, and other geometric shapes.

The distal stanchion 272 can also define a keyed portion 276. The inclusion of a second keyed portion 276 is considered advantageous at least because it provides for additional contact and engagement with an insertion tool. If included, the keyed portion 276 of the distal stanchion 272 can have any suitable size and configuration and a skilled artisan will be able to select an appropriate size and configuration for a medical device according to a particular embodiment based on various considerations, including the configuration of any insertion tool with which the medical device will be used. In the illustrated embodiment, the keyed portion 276 defines a square-shaped opening 277 and recess. While the square-shaped opening 277 and recess defined by the distal stanchion 272 is similar in size and configuration to the square-shaped opening 275 defined by the proximal stanchion 270, it is noted that, if two keyed portions are included in a medical device according to a particular embodiment, the keyed portions can define openings and recesses that have the same or different sizes and that have the same or different configurations. For example, the keyed portion 274 defined by the proximal stanchion 270 can define a square-shaped opening and recess while the keyed portion defined by the distal stanchion 272 can define an opening and recess having a differently sized and configured opening, such as a triangular-shaped opening or a square-shaped opening having a different size.

Figure 4:
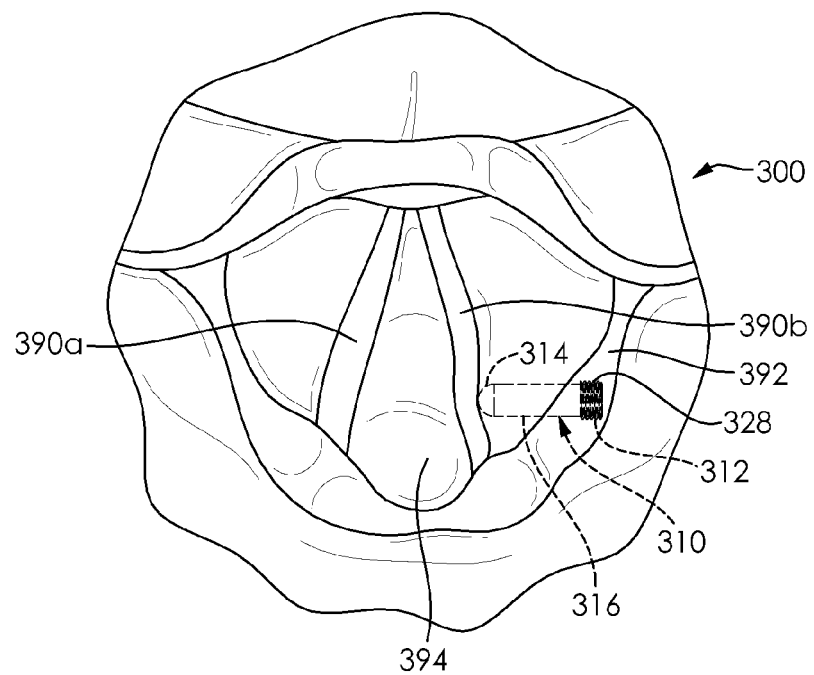
FIG. 4 is a sectional view of an airway of a patient, within which an exemplary medical device has been implanted.

FIG. 4 illustrates an exemplary medical device 310 according to the disclosure disposed within an airway 300 of a patient. The patient has two vocal cords—healthy vocal cord 390a and paralyzed vocal cord 390b. The medical device 310 has been positioned to interact with paralyzed vocal cord 390b by securing the proximal portion 312 of the medical device 310 within the thyroid cartilage 392. This has been accomplished by threading the proximal portion 312 through the cartilage using the thread 328 defined by the proximal portion 312. A portion of the main body 316 of the medical device 310 extends into the larynx 394 of the patient. In this manner, the distal portion 314 of the medical device 310 is positioned such that it is in contact with the paralyzed vocal cord 390b. As illustrated in the Figure, this placement of the medical device 310 provides the desired medialization of the paralyzed vocal cord 390b.

Figure 5:
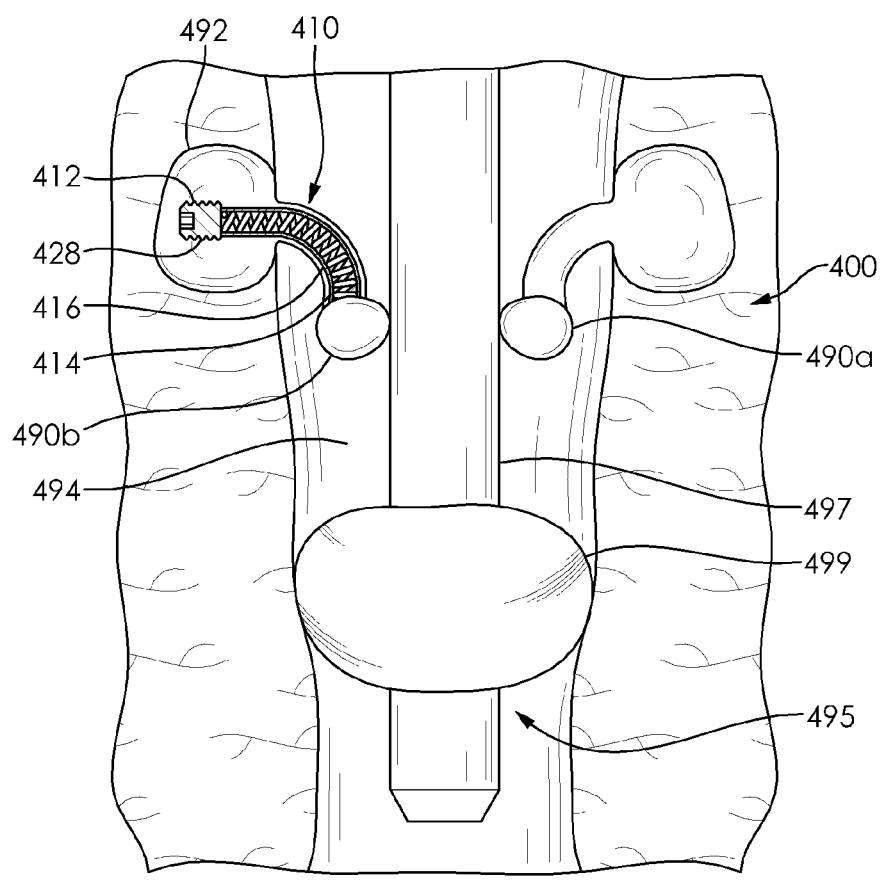
FIG. 5 is a sectional view of an airway of a patient, within which the medical device illustrated in FIG. 3 has been implanted and into which a conduit has been inserted.

FIG. 5 illustrates an exemplary medical device 410 according to the disclosure disposed within airway 400 of a patient. Similar to the airway illustrated in FIG. 4, the patient has two vocal cords—healthy vocal cord 490a and paralyzed vocal cord 490b. The medical device 410 has been positioned to interact with paralyzed vocal cord 490b by securing the proximal portion 412 of the medical device 410 within the thyroid cartilage 492. This has been accomplished by threading the proximal portion 412 through the cartilage 492 using the thread 428 defined by the proximal portion 412. A portion of the main body 416 of the medical device 410 extends into the larynx 494 of the patient. In this manner, the distal portion 414 of the medical device 410 is positioned such that it is in contact with the paralyzed vocal cord 490b.

FIG. 5 illustrates the ability of the medical device 410 to deflect upon passage of another medical device into the airway of the patient. In this figure, intubation device 495 has been inserted into the airway 400. Intubation device 495 includes tubular member 497 and inflatable balloon 499. As illustrated, medical device 410 is in a deflected configuration as a result of the passage of intubation device 495 through the vocal cords 490a, 490b. Upon retraction of intubation device 495, medical device 410 returns to its previous position in which paralyzed vocal cord 490b is in the desired medialized position. The flexible nature of the main body 416 of medical device 410 provides this desired responsiveness of medical device 410.

The inventive medical devices can be implanted using any suitable technique and procedure, and implantation can be accomplished with or without the use of additional devices, such as an insertion tool. Skilled artisans will be able to determine an appropriate technique and/or procedure, and whether an additional device or devices is/are needed, based on various considerations, including the ease of access to the target implant site, the extent to which the medical device needs to extend into the larynx of the patient, and other various considerations.

Figures 6, 6A:
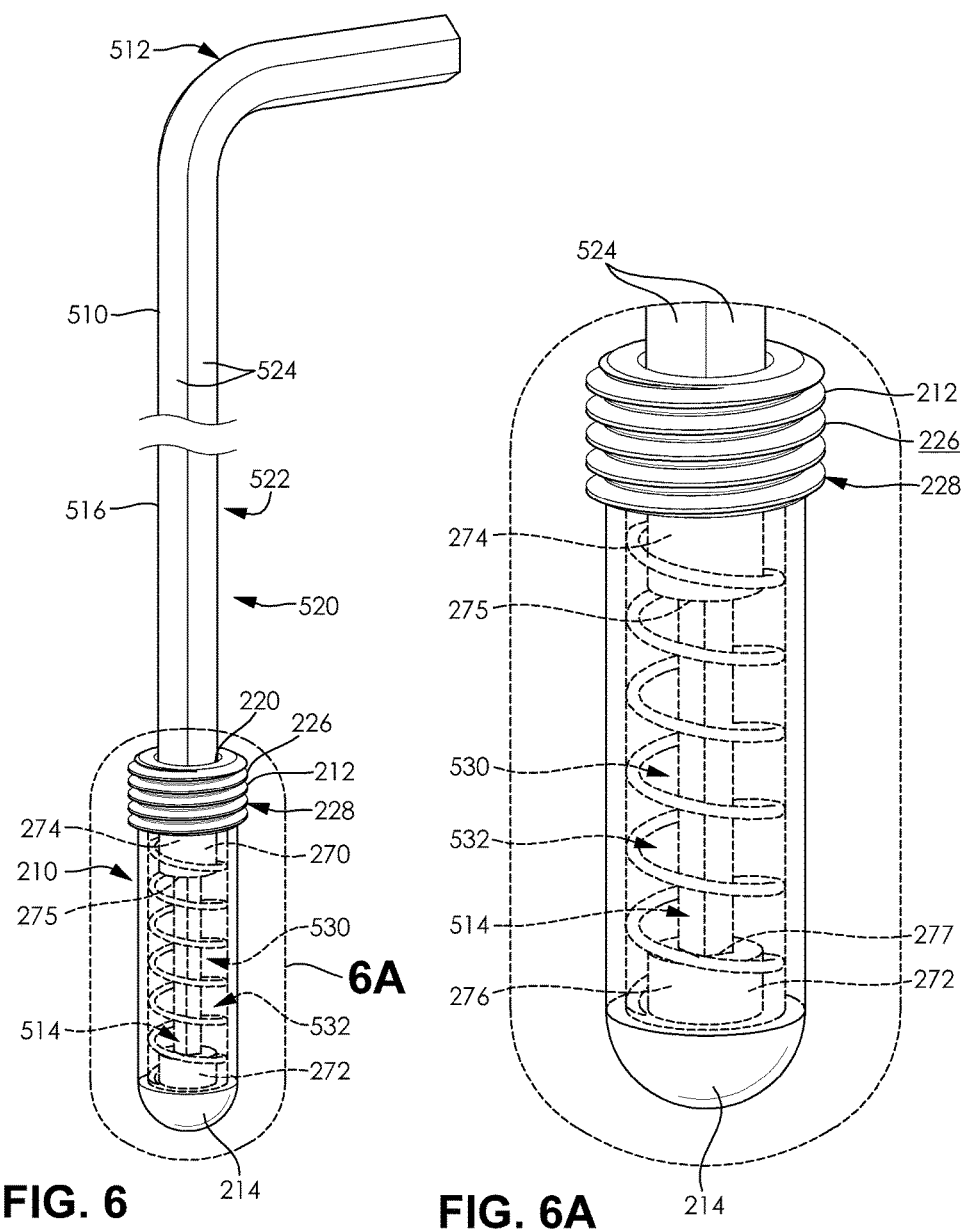
FIG. 6 is a perspective view of an implant assembly including the medical device illustrated in FIG. 3 and an engaged insertion tool.
FIG. 6A is a magnified view of area 6A indicated in FIG. 6.

FIGS. 6 and 6A illustrate a first exemplary insertion tool 510 that is suitable for use with medical devices according to some embodiments. In the Figures, insertion tool 510 illustrated in use with medical device 210 illustrated in FIGS. 3, 3A, 3B and 3C.

Insertion tool 510 is a solid member having a proximal end 512, a distal end 514, and a main body 516 extending between the proximal 512 and distal 514 ends. The main body 516 defines a first keyed portion 520 and a second keyed portion 530. The first keyed portion 520 is sized and configured to pass through the proximal passageway 220 of the proximal portion 212 of medical device 210 while also being able to engage the inner surface (not illustrated in FIGS. 6 and 6A) of the proximal portion 212. For example, in the illustrated embodiment, first keyed portion 520 has a hexagonal cross-sectional shape 522 that is sized and configured to pass through proximal passageway 220 of proximal portion 212 of medical device 210 upon axially-directed movement of the main body 516 along the longitudinal axis of medical device 210, while also being able to engage the inner surface (not illustrated in FIGS. 6 and 6A) of proximal portion 212, such as by contact between one or more of outer facets 524 and one or more facets (not illustrated in FIGS. 6 and 6A) of the inner surface (not illustrated in FIGS. 6 and 6A) of proximal portion 212, upon rotationally-directed movement of main body 516 about the longitudinal axis of the main body 516 and/or of the medical device 210. The structure and function allows insertion tool 510 to both axially advance medical device 210 through an opening in tissue and also to secure the medical device 210 in the tissue defining the opening, such as by threading the thread 228 defined by outer surface 226 of proximal portion 212 through the tissue.

The second keyed portion 530 is sized and configured to pass through the opening 275 defined by the keyed portion 274 of the proximal stanchion 270 while also being able to engage the inner surface of the opening 275. For example, the second keyed portion 530 in the illustrated insertion tool 510 has a square-shaped cross-sectional profile that is sized and configured for passage through opening 275 defined by proximal stanchion 270. Furthermore, upon rotationally-directed movement of main body 516 about the longitudinal axis of the main body 516 and/or of the medical device 210, the square-shaped cross-sectional profile of the second keyed portion 530 is able to engage the inner surface (not illustrated in FIGS. 6 and 6A) of the opening 275 defined by the proximal stanchion 270.

In the illustrated embodiment, second keyed portion 530 is also sized and configured to pass into the opening 277 defined by the keyed portion 276 of the distal stanchion 272 while also being able to engage the inner surface (not illustrated in FIGS. 6 and 6A) of the opening 277. While this configuration and function of the second keyed portion 530 is optional, it is considered advantageous at least because it is expected to distribute torque generated during rotationally-directed movement of the main body 516 across a length of the medical device 210. This distribution of force can avoid bunching, creasing, and/or other distortion of the main body 216 of the medical device 210 during implantation.

While the illustrated insertion tool 510 has a hexagonal cross-sectional shape 522 and a square cross-sectional shape 532, the insertion tool 510 can have any combination of suitable sizes and cross-sectional shapes and configurations for the first 520 and second 530 keyed portions. To facilitate use with a medical device, the first keyed portion 520 should be sized and configured to enable the desired structural interaction with the proximal portion of the relevant medical device, as described above. If included, the second keyed portion 530 should be sized and configured to enable the structural interaction with the distal portion of the relevant medical device, as described above. Furthermore, while the illustrated insertion tool 510 has first 520 and second 530 keyed portions that have different sizes and configurations, the second keyed portion of an insertion tool, if present, can have the same or different size and configuration as the first keyed portion. Ultimately, an insertion tool according to a particular embodiment should have a first keyed portion adapted for passage through and engagement with a proximal passageway of a relevant medical device. The optional second keyed portion, if included, should be adapted for passage into and engagement with an opening defined by a distal portion of the relevant medical device.

Insertion tools can include various modifications to facilitate implantation of the inventive medical devices. For example, FIG. 7 illustrates a second exemplary insertion tool 610 that has been modified to facilitate visualization of the implant site during placement of a medical device. The insertion tool 610 is similar to insertion tool 510 illustrated in FIGS. 6 and 6A, except as described below. Thus, insertion tool 610 has a proximal end 612, a distal end 614, and a main body 616 extending between the proximal 612 and distal 614 ends. The main body 616 defines a first keyed portion 620 and a second keyed portion 630.

In this embodiment, the insertion tool 610 defines a passageway 650 that extends through a portion of the insertion tool 610. An optical element, such as fiber optic 652, is disposed within the passageway 650. The passageway 650 opens to the distal end 614 of the insertion tool 610 to allow light emitting from the fiber optic 652 to emit from the distal end 614 of the insertion tool 610. To facilitate use with the insertion tool, medical device 210 includes alternative distal portion to 214' that is translucent or transparent. The fiber optic 652 can be connected to a light source such that light travels through the fiber optic 652 and emits from the insertion tool 610 and, when engaged with medical device 210, such as illustrated in FIG. 7, from the distal portion 214' of the medical device 210. A user can use the light emitted from the insertion tool 610 and medical device 210 to visualize the implant site prior to inserting the medical device 210.

The various medical devices and/or insertion tools can be placed into a container to form a medical device kit useful in the treatment of vocal cord paralysis. For example, two or more medical devices can be placed into a container to form a medical device kit useful in the treatment of patients suffering paralysis of both vocal cords. Furthermore, a medical device and an insertion tool can be placed into a container to form a medical device kit useful in the treatment of a patient suffering from vocal cord paralysis. In these kits, the medical device can be positioned independent of the insertion tool or engaged with the insertion tool. For example, the insertion tool can be positioned with the first keyed portion pre-placed through the proximal passageway of the medical device. If included, a second keyed portion of the insertion tool can be pre-placed into an opening defined by a distal stanchion of the medical device. This engagement within the kit is considered advantageous at least because it eliminates the need to engage the medical device with the insertion tool immediately prior to use and because it helps to ensure use of a properly-sized insertion tool with the medical device included in the kit.

FIG. 8 illustrates an exemplary method 700 of treating vocal cord paralysis. A first step 702 comprises inserting a medical device according to an embodiment of the invention into the larynx of a patient having a paralyzed vocal cord. The medical device can comprise any medical device according to any embodiment of the invention, including each of the embodiments described and/or illustrated herein and all embodiments within the scope of the claims. This step 702 can comprise inserting the medical device through an opening, natural or artificially created, in the thyroid cartilage.

A second step 704 comprises securing the medical device that has been inserted into the larynx of the patient to the thyroid cartilage. This step can comprise threading a thread defined by a portion of the medical device through the thyroid cartilage. This step 704 can be conducted such that the medical device advances toward and contacts the paralyzed vocal cord. Furthermore, this step should be conducted to a degree that produces a desired degree of medialization of the vocal cord. For example, a clinician can have a patient phonate while performing this step until a desired vocal sound is achieved. An insertion tool, such as the insertion tools described and/or illustrated herein, can be used in the performance of this step.

The foregoing detailed description refers to exemplary medical devices and includes the best mode for practicing the invention. The description and the appended drawings illustrating the described devices are intended only to provide examples and not to limit the scope of the claims in any manner.

What is claimed is:

1. A method of treating a paralyzed vocal cord, the method comprising the steps of:
   inserting a medical device through an opening in thyroid cartilage;
   positioning the medical device such that it interacts with said paralyzed vocal cord; and
   securing the medical device to the thyroid cartilage using an insertion tool, the insertion tool defining a passageway extending through a portion of the insertion tool;
   further comprising a fiber optic disposed within the passageway defined by the insertion tool.

2. A method of treating a paralyzed vocal cord, the method comprising the steps of:
   inserting a medical device through an artificial opening created in thyroid cartilage;
   positioning the medical device such that it interacts with said paralyzed vocal cord; and
   securing the medical device to the thyroid cartilage using an insertion tool, the insertion tool having a distal end and defining a passageway extending through a portion of the insertion tool, the passageway defined by an insertion tool opening at the distal end of the insertion tool;
   further comprising a fiber optic disposed within the passageway defined by the insertion tool.

* * * * *